US009913609B2

(12) United States Patent
Hirano

(10) Patent No.: US 9,913,609 B2
(45) Date of Patent: Mar. 13, 2018

(54) MOBILE ELECTRONIC DEVICE, NON-TRANSITORY STORAGE MEDIUM STORING DIAGNOSIS PROGRAM, AND DIAGNOSIS SYSTEM

(71) Applicant: KYOCERA Corporation, Kyoto-shi, Kyoto (JP)

(72) Inventor: Asao Hirano, Koganei (JP)

(73) Assignee: KYOCERA CORPORATION, Kyoto (JP)

( * ) Notice: Subject to any disclaimer, the term of this patent is extended or adjusted under 35 U.S.C. 154(b) by 231 days.

(21) Appl. No.: 14/761,611

(22) PCT Filed: Jan. 17, 2014

(86) PCT No.: PCT/JP2014/050799
§ 371 (c)(1),
(2) Date: Jul. 16, 2015

(87) PCT Pub. No.: WO2014/115652
PCT Pub. Date: Jul. 31, 2014

(65) Prior Publication Data
US 2015/0359476 A1    Dec. 17, 2015

(30) Foreign Application Priority Data

Jan. 23, 2013 (JP) ................................ 2013-010299

(51) Int. Cl.
*A61B 5/026* (2006.01)
*A61B 5/00* (2006.01)
(Continued)

(52) U.S. Cl.
CPC ........ *A61B 5/4035* (2013.01); *A61B 5/02405* (2013.01); *A61B 5/6898* (2013.01);
(Continued)

(58) Field of Classification Search
CPC . A61B 5/4035; A61B 5/02405; A61B 5/6898; A61B 5/7203; A61B 5/721;
(Continued)

(56) References Cited

U.S. PATENT DOCUMENTS 5,299,119 A * 3/1994 Kraf .................... A61B 5/0452
128/905
6,490,480 B1 * 12/2002 Lerner ................. A61B 5/0531
600/547

(Continued)

FOREIGN PATENT DOCUMENTS

EP      1908402 A1    4/2008
JP   2008-253579 A   10/2008
(Continued)

OTHER PUBLICATIONS

Extended European Search Report in EP Application No. 14742733.0, dated Sep. 6, 2016.
(Continued)

*Primary Examiner* — Navin Natnithithadha
(74) *Attorney, Agent, or Firm* — Hauptmah Ham, LLP

(57) ABSTRACT

A mobile electronic device includes: waveform information acquisition part configured to add a time stamp to a waveform detected from a user and record the waveform with the time stamp as waveform information; condition information acquisition part configured to add a time stamp to information indicating a condition of the user and record the information with the time stamp as condition information; artifact waveform acquisition part configured to acquire, from artifact waveform data in which a condition and the artifact waveform are associated with each other and stored, an artifact waveform that corresponds a condition indicated by the condition information in the same time period as a time period of the waveform information; waveform correction part configured to correct the waveform information
(Continued)

using the artifact waveform; and autonomic nerves diagnosis part configured to diagnose autonomic nerves of the user using the waveform information corrected by the waveform correction part.

20 Claims, 6 Drawing Sheets

(51) Int. Cl.
    *A61B 5/024*     (2006.01)
    *A61B 5/11*     (2006.01)

(52) U.S. Cl.
    CPC .............. *A61B 5/721* (2013.01); *A61B 5/7203* (2013.01); *A61B 5/7278* (2013.01); *A61B 5/026* (2013.01); *A61B 5/02416* (2013.01); *A61B 5/02438* (2013.01); *A61B 5/1112* (2013.01); *A61B 5/1123* (2013.01); *A61B 5/7282* (2013.01); *A61B 2560/0247* (2013.01); *A61B 2560/0252* (2013.01); *A61B 2560/0257* (2013.01); *A61B 2560/0443* (2013.01); *A61B 2562/0219* (2013.01)

(58) Field of Classification Search
    CPC .............. A61B 5/7278; A61B 5/02416; A61B 5/02438; A61B 5/026; A61B 5/1112; A61B 5/1123; A61B 5/7282; A61B 2560/0247; A61B 2560/0252; A61B 2560/0257; A61B 2560/0443; A61B 2562/0219
    USPC .......................... 600/500–503, 481, 483, 485
    See application file for complete search history.

(56) References Cited

U.S. PATENT DOCUMENTS

| | | | | |
|---|---|---|---|---|
| 6,496,723 | B1* | 12/2002 | Kawachi | A61B 5/02422 600/517 |
| 6,669,645 | B2* | 12/2003 | Narimatsu | A61B 5/4035 600/481 |
| 7,727,158 | B2* | 6/2010 | Kitajima | A61B 5/02416 600/485 |
| 8,740,806 | B2* | 6/2014 | Parfenova | A61B 5/4818 600/484 |
| 8,801,621 | B2 | 8/2014 | Kitajima et al. | |
| 9,173,579 | B2* | 11/2015 | Berkow | A61B 5/02028 |
| 2004/0127950 | A1 | 7/2004 | Kim et al. | |
| 2009/0082681 | A1* | 3/2009 | Yokoyama | A61B 5/024 600/509 |
| 2010/0125215 | A1* | 5/2010 | Kuo | A61B 5/0006 600/509 |
| 2012/0029374 | A1* | 2/2012 | Berkow | A61B 5/02028 600/526 |
| 2012/0203076 | A1* | 8/2012 | Fatta | A61B 5/681 600/300 |
| 2014/0128697 | A1* | 5/2014 | Parfenova | A61B 5/4818 600/328 |

FOREIGN PATENT DOCUMENTS

| | | |
|---|---|---|
| JP | 2009-297233 A | 12/2009 |
| JP | 2013-233204 A | 11/2013 |

OTHER PUBLICATIONS

International Search Report dated Feb. 25, 2014 in corresponding International Application No. PCT/JP2014/050799.

* cited by examiner

MOBILE ELECTRONIC DEVICE, NON-TRANSITORY STORAGE MEDIUM STORING DIAGNOSIS PROGRAM, AND DIAGNOSIS SYSTEM

RELATED APPLICATIONS

The present application is a National Phase entry of International Application No. PCT/JP2014/050799, filed Jan. 17, 2014, which claims priority of Japanese Application No. 2013-010299, filed Jan. 23, 2013.

FIELD

The present application relates to a mobile electronic device, a diagnosis method and diagnosis program.

BACKGROUND

Several kinds of art for detecting or diagnosing a condition of a human body are known. For example, Patent literature 1 discloses a technique to calculate a pulse wave based on an input image that has been captured by laying a finger on a lens of a camera. Patent literature 2 discloses a technique that the pulse wave data of a subject to be diagnosed from which a noise such a dysrhythmia is removed is employed in order to diagnose autonomic nerves and the like of the subject.

CITATION LIST

Patent Literature

Patent Literature 1: Japanese Laid-open Patent Publication No. 2009-297233
Patent Literature 2: Japanese Laid-open Patent Publication No. 2008-253579

Technical Problem

In a case of diagnosing the autonomic nerves, it is difficult to make a precise diagnosis because the autonomic nerves are likely sensitive to various kinds of factors. In particular, in a case of diagnosing the autonomic nerves of the subject who is moving with a mobile electronic device, it is difficult to make a precise diagnosis due to a large change of a condition. In this regard, there is a need for providing a mobile electronic device, a diagnosis method and diagnosis program which can improve an accuracy of diagnosis of the autonomic nerves.

SUMMARY

According to one of aspects, there is provided a mobile electronic device including: waveform information acquisition part configured to add a time stamp to a waveform detected from a user and record the waveform with the time stamp as waveform information; condition information acquisition part configured to add a time stamp to information indicating a condition of the user and record the information with the time stamp as condition information; artifact waveform acquisition part configured to acquire, from artifact waveform data in which a condition and an artifact waveform are associated with each other and stored, the artifact waveform that corresponds a condition indicated by the condition information within the same time period as a time period of the waveform information; waveform correction part configured to correct the waveform information using the artifact waveform; and autonomic nerves diagnosis part configured to diagnose autonomic nerves of the user using the waveform information corrected by the waveform correction part.

According to one of aspects, there is provided a diagnosis system, comprising: a memory configured to store an artifact waveform data in which an activity information indicating an activity status of a person and an artifact waveform ascribed to the activity status indicated by the activity information are associated with each other; and a controller communicatively or electronically coupled to the memory. The controller is configured to: add a time stamp to a waveform detected from a user in a predetermined time period to obtain a stamped waveform information, add another time stamp to activity information indicating an activity status of the user in the predetermined time period to obtain a stamped activity information, acquire, from the artifact waveform data, the artifact waveform that corresponds to the activity information indicating the activity status indicated by the stamped activity information, correct the stamped waveform information using the artifact waveform acquired from the artifact waveform data to obtain corrected waveform information, and diagnose autonomic nerves of the user using the corrected waveform information.

According to one of aspects, there is provided a program causing a mobile electronic device to execute: adding a time stamp to a waveform detected from a user and recording the waveform with the time stamp as waveform information; adding a time stamp to information indicating a condition of the user and recording the information with the time stamp as condition information; acquiring, from artifact waveform data in which a condition and the artifact waveform are associated with each other and stored, an artifact waveform that corresponds a condition indicated by the condition information in the same time period as a time period of the waveform information; correcting the waveform information using the artifact waveform; and diagnosing autonomic nerves of the user using the corrected waveform information.

DESCRIPTION OF EMBODIMENTS

The embodiment for carrying out the present invention is described in detail with reference to the drawings attached hereto.

Figure 1:
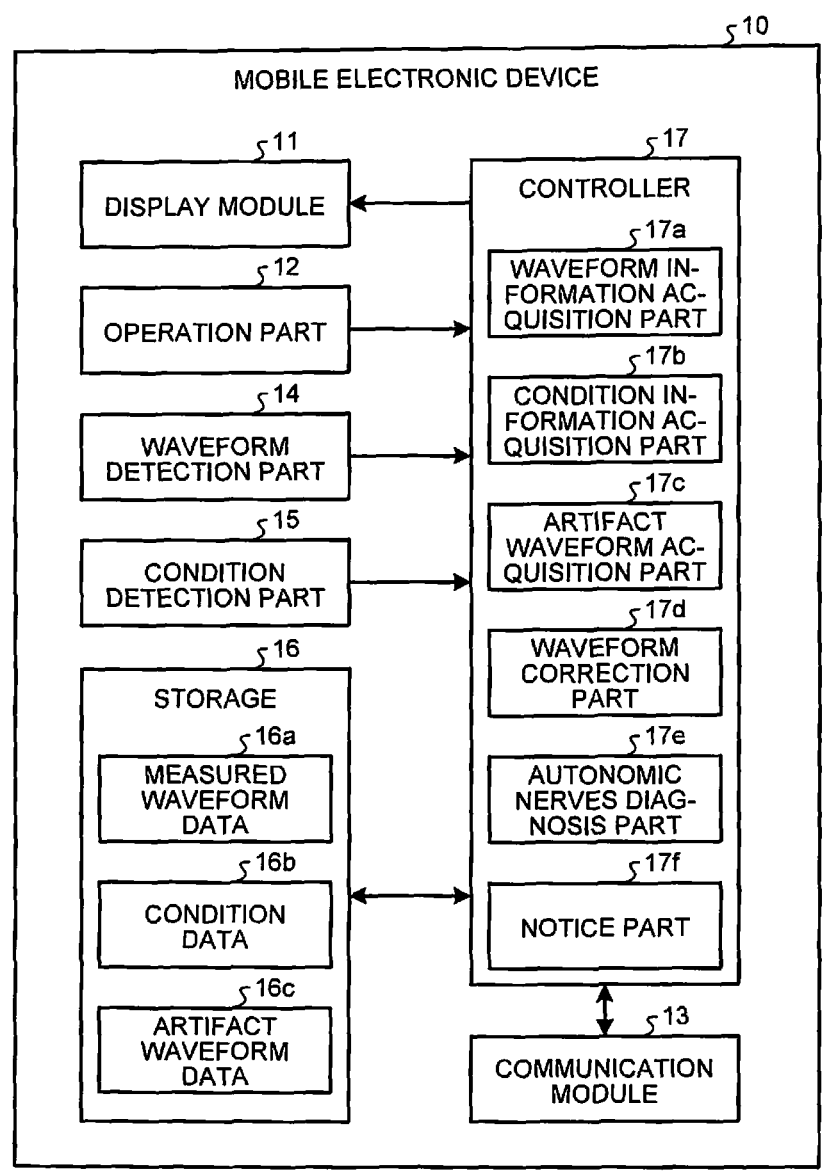
FIG. 1 is a block diagram of a mobile electronic device.

Referring to FIG. 1, a configuration of a mobile electronic device 10 according to the embodiment is described. FIG. 1 is a block diagram of the mobile electronic device 10. The mobile electronic device 10, for example, is a mobile phone. The mobile electronic device 10 has a function to diagnose autonomic nerves of a subject. As shown in FIG. 1, the mobile electronic device 10 includes a display module 11, an operation part 12, a communication module 13, a waveform detection part 14, a condition detection part 15, a storage 16 and a controller 17.

The display module 11 is provided with a display device such a Liquid Crystal Display (LCD), an Organic Electro-Luminescence Display (OELD) or an Inorganic Electro-Luminescence Display (IELD). The display module 11 displays a screen that includes characters, images, symbols, diagrams and the like.

The operation part 12 receives an operation conducted by a user. The operation part 12 is provided with an input device such a button, a key, a touch screen or the like. The operation part 12 may be integrally formed together with the display module 11 like a touch screen display.

The communication module 13 performs a wireless communication. The communication module 13 supports a seller phone communication such a 2G, 3G, 4G and the like, for example. The communication module 13 may support a plurality of communication protocol. The communication module 13 may support a short range communication protocol such an IEEE 802.11, Bluetooth™ or the like.

The waveform detection part 14 detects a waveform to diagnose the autonomic nerves of the user who is carrying the mobile electronic device 10. The waveform to diagnose the autonomic nerves of the user includes for example a waveform of the pulse wave, a waveform indicating a variation of a heart rate, and the like.

The waveform detection part 14 can include various kinds of sensors. In a case that a waveform of the pulse wave is employed as a waveform to diagnose the autonomic nerves of the user, the waveform detection part 14 can include a camera (e.g., image sensor), for example. In a case that a waveform indicating a variation of a heart rate is employed as a waveform to diagnose the autonomic nerves of the user, the waveform detection part 14 can include a small heat rate sensor or a photoelectric pulse wave counter, for example.

The waveform detection part 14 may include a sensor other than the above mentioned one. The waveform detection part 14 may include a plurality of sensors to detect a waveform and may be configured to be capable of selecting an optimal waveform depending on a condition. A sensor of the waveform detection part 14 may be used for a purpose other than diagnosis of the autonomic nerves of the user. In other words, a sensor that the mobile electronic device 10 is provided with for other purpose may be also used as the waveform detection part 14. In the following description, it is assumed that a waveform of a pulse wave is used as a waveform to diagnose the autonomic nerves of the user.

The condition detection part 15 detects a condition of the user who is carrying the mobile electronic device 10. The condition detection part 15 can include various kinds of sensors.

The condition detection part 15 can include an acceleration sensor. The acceleration sensor allows to detect a direction and a magnitude of an acceleration applied to the user. Furthermore, analyzing the direction and the magnitude of the acceleration allows for foreseeing a moving condition of the user, a magnitude of oscillation the user are encountering, and the like. Moving condition that is foreseeable includes a static condition, a walking condition, a running condition, a riding condition, and the like.

The condition detection part 15 can include a barometer. The barometer allows for a detection of a variation of an atmospheric pressure around the user. The variation of the atmospheric pressure can be used in order to foresee an attitude of where the user currently is. It is possible to foresee a condition in which the user is going up or going down a slope, for example. As a result, an accuracy of foresee of moving condition of the user is improved.

The condition detection part 15 can include a Global Positioning System (GPS) receiver. The GPS receiver allows for a detection of the current position of the user. It is possible to foresee how environment the user is with a high accuracy by matching a current position to a map data. It is possible to determine whether the user moves along a road or a rail, and thus identify a kind of a ride. As a result, an accuracy of foresee of moving condition of the user is improved.

The condition detection part 15 can include an illuminance sensor. The illuminance sensor allows for a detection of brightness around the user. The condition detection part 15 can include a temperature sensor. The temperature sensor allows for a detection of a temperature around the user. The condition detection part 15 can include an electrostatic capacitive touch sensor. The electrostatic capacitive touch sensor allows for a detection of a magnitude of a capacitance of the user's body. It is possible to use the magnitude of a capacitance in order to foresee a tension of the user.

The condition detection part 15 may include a sensor other than the above mentioned one. The condition detection part 15 may include a plurality of sensors. A sensor of the condition detection part 15 may be used for a purpose other than diagnosis of the autonomic nerves of the user. In other words, a sensor that the mobile electronic device 10 is provided with for other purpose may be also used as the condition detection part 15.

A storage 16 stores a program and data. The storage 16 is also utilized as a working area to temporally store the result of a process of a controller 17. The storage 16 may include any non-transitory memory medium such as a semiconductor memory medium, a magnetic memory medium. The storage 16 may include a plurality of memory mediums. The storage 16 may include a combination of a general purpose non-transitory memory medium such as a memory card, an optical disk, or an optical magnetic disk and a reading device of the memory medium. The storage 16 may include a memory device that is used as a temporal memory area such a Random Access Memory (RAM).

The storage 16 stores data including the measured waveform data 16a, condition data 16b, and artifact waveform data 16c. In the measured waveform data 16a, a waveform detected by the waveform detection part 14 is recorded as waveform information. In the condition data 16b, information indicating a condition of the user detected by the condition detection part 15 is recorded as condition information. Time stamp for indicating a detected time is added to the waveform information recorded in the measured waveform data 16a and the condition information recorded in the condition data 16b such that both information can be processed in synchronization with each other.

In the artifact waveform data 16c, an artifact of a waveform ascribed to the condition (hereinafter, referred to as "artifact waveform") is recorded in association with a condition information indicating the condition of the user. The artifact waveform is a difference between a waveform to be normally detected and a waveform that has changed according to the condition. In other word, the artifact waveform is a noise component (artifact component) that prevents an improvement of an accuracy of the diagnosis of the autonomic nerves.

A combination of the condition information and the artifact waveform are stored in the artifact waveform data 16c in advance. The combination of the condition information and the artifact waveform can be obtained, for example, by comparing waveforms detected from the subject under various conditions.

The artifact waveform data 16c may configured such that the artifact waveform is associated with a plurality kinds of condition information that have been detected in the same time period and under the same condition.

The controller 17 generally controls a mobile electronic device 10. The controller 17 performs various controls so that the mobile electronic device 10 exerts functions appropriately. The controller 17 includes an arithmetic processing unit. The arithmetic processing unit is a Central Processing Unit (CPU), a System-on-a-chip (SoC), a Micro Control Unit (MCU), or a Field-Programmable Gate Array (FPGA) for example.

The controller 17 includes a waveform information acquisition part 17a, a status information acquisition part 17b, an artifact waveform acquisition part 17c, a waveform correction part 17d, an autonomic nerves diagnosis part 17e, and a notice part 17f. The waveform information acquisition part 17a acquires a waveform that has been detected by the waveform detection part 14 and adds a time stamp thereto and records it as waveform information into the measured waveform data 16a.

The status information acquisition part 17b acquires information indicating a condition of the user from the condition detection part 15 and adds a time stamp thereto and records it as condition information into the condition data 16b. The status information acquisition part 17b may record information acquired from the condition detection part 15 as condition information into the condition data 16b without changing the information and record information obtained by analyzing information acquired from the condition detection part 15 as condition information into the condition data 16b. An example is described below, where the condition detection part 15 includes a accelerate sensor. In a case that acquired information is recorded without changing, a direction and a magnitude of the acceleration are recorded as condition information. On the other hand, in a case that information obtained by analyzing acquired information is recorded, moving condition of the user foreseen based on a direction and a magnitude of the acceleration is recorded as condition information.

The artifact waveform acquisition part 17c acquires an artifact waveform from the artifact waveform data 16c, the artifact waveform corresponding to a designated condition information. The artifact waveform acquisition part 17c specifies condition information, which is the closest to a designated condition information, from among condition information stored in the artifact waveform data 16c so as to acquire an artifact waveform that corresponds to the designated condition information. Furthermore, the artifact waveform acquisition part 17c acquires an artifact waveform that has been associated with the specified condition information from the artifact waveform data 16c. Specifying the closest condition information is accomplished by such a statistic method as a moving-average method.

In a case that an artifact waveform is associated with a plurality kinds of condition information, the artifact waveform acquisition part 17c may determine a priority for each kinds of condition information so as to specify condition information which is the closest to a designated condition information, based on the priority. For example, a method may be employed for evaluating an approximation of condition information having higher priority in order so as to narrow a combination of condition information and an artifact waveform. Alternatively, a method may be employed for multiplying approximate value that has been evaluated for condition information by a weight allocated to each of priorities of condition information so as to calculate a total approximation value of a combination of condition information and an artifact waveform.

The waveform correction part 17d corrects a waveform indicated by waveform information included in the measured waveform data 16a using an artifact waveform acquired by the artifact waveform acquisition part 17c. Correction using the artifact waveform allows for a removal of a noise component due to a condition of the user from waveform information included in the measured waveform data 16a. In this way, it is possible to improve an accuracy of diagnosis of autonomic nerves on a basis of waveform information.

The waveform correction part 17d corrects a waveform by means of waveform separation. Specifically, the waveform correction part 17d corrects waveform information by subtracting an artifact waveform from a waveform indicated by waveform information included in the measured waveform data 16a.

prior to a correction using an artifact waveform, the waveform correction part 17d adjusts a scale of each of amplitude and a wavelength of an artifact waveform so as to meet a scale of that of a waveform indicated by waveform information included in the measured waveform data 16a. It is not necessary that a kind of a sensor included in the waveform detection part 14 is identical to that of a sensor used to obtain an artifact waveform. It is not necessary that the subject from whom an artifact waveform is to be acquired is identical to the user of the mobile electronic device 10.

The waveform correction part 17d adjusts a scale of the amplitude of an artifact waveform using a predetermined coefficient. The coefficient is determined based on a difference of a sensibility between sensors, a difference of an output level between sensors, or the like.

The waveform correction part 17d calculates a singular point of an artifact waveform and a singular point of a waveform included in the measured waveform data 16a in order to adjust a scale of a wavelength of the artifact waveform. The singular point can be calculated using a Fourier transformation, a fast Fourier transformation, a wavelet transformation, and the like, for example. The waveform correction part 17d adjusts a scale of a wavelength of an artifact waveform such that the singular point of the artifact waveform best matches that of a waveform included in the measured waveform data 16a.

The autonomic nerves diagnosis part 17e diagnoses autonomic nerves of the user on a basis of a waveform information corrected by the waveform correction part 17d. As a method of diagnosing autonomic nerves, various known arts are available.

The notice part 17f notifies the user of a result of a diagnosis performed by the autonomic nerves diagnosis part 17e. The notice part 17f notifies the user of the result of a diagnosis by displaying it at the display module 11, for example. Any method of notifying the user of a result of the diagnosis can be employed. The notice part 17f may have a function to process the result of the diagnosis of autonomic nerves for each of application usages. For example, the notice part 17f can incorporate a plugin for an application that is downloaded by the user from a commercial server through the communication module 13. The plugin allows the notice part 17f to change a form of a result of a diagnosis to be displayed and the like.

Figure 2:
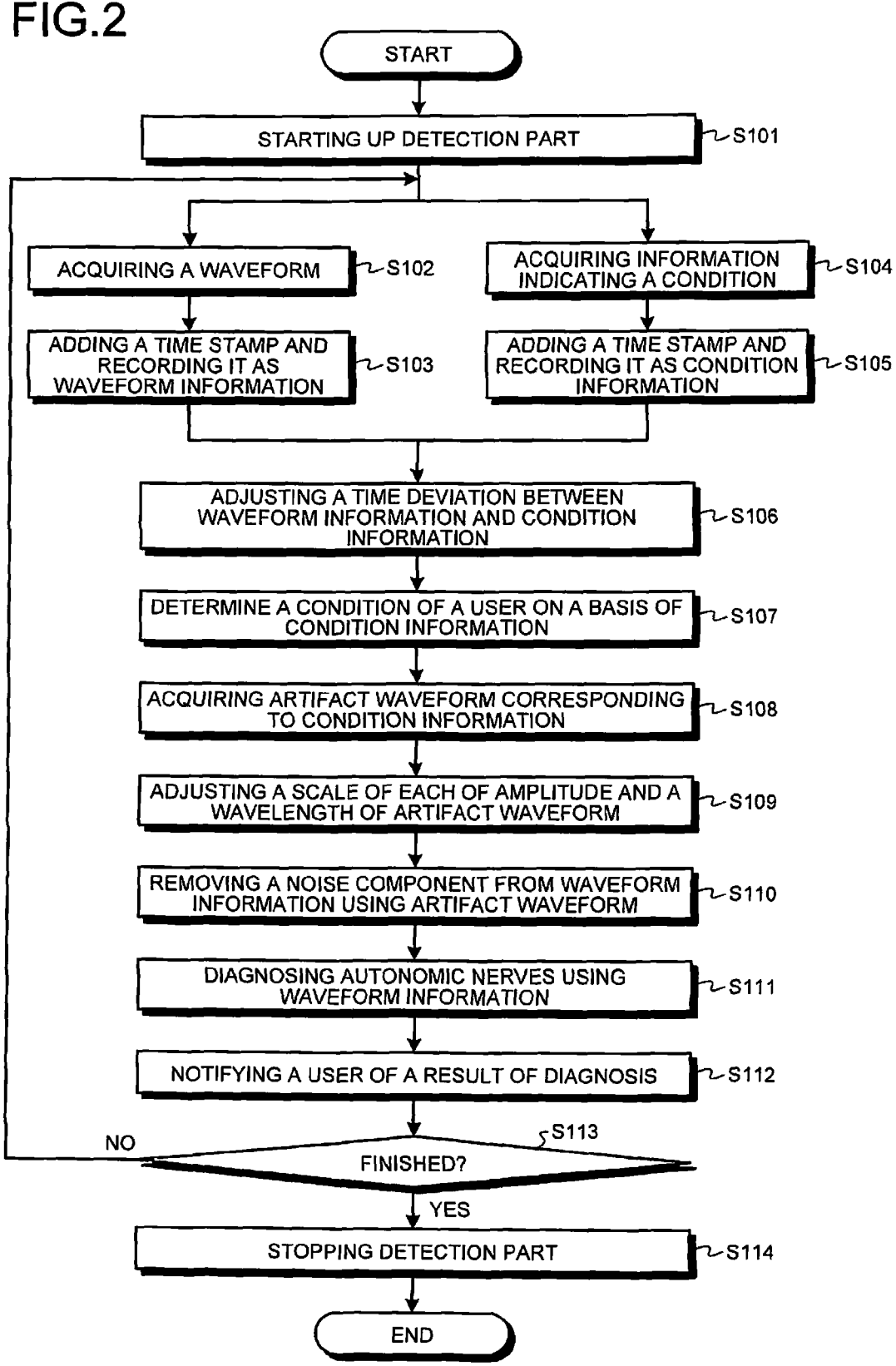
FIG. 2 is a flowchart illustrating an exemplary procedure of a diagnosis process of the autonomic nerves.
Figure 3:
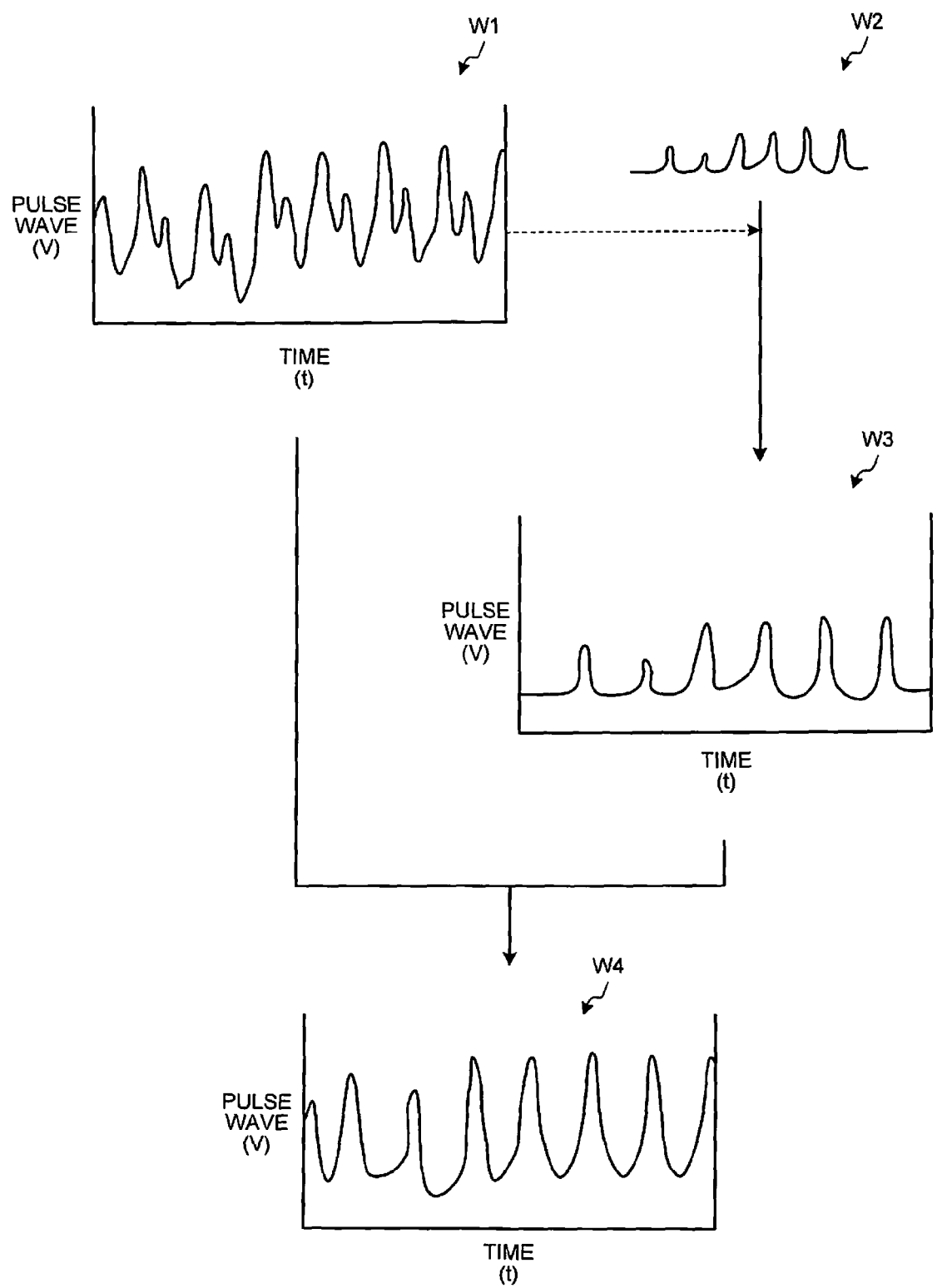
FIG. 3 is a diagram illustrating an exemplary waveform to be processed by the mobile electronic device.

Referring to FIGS. 2 and 3, diagnosis process of autonomic nerves using the mobile electronic device 10 is described below. FIG. 2 is a flowchart illustrating an exemplary procedure of diagnosis process of autonomic nerves. FIG. 3 is a diagram illustrating an exemplary waveform to be processed by the mobile electronic device 10.

As shown in FIG. 2, the controller 17 in a step S101 starts up the waveform detection part 14 and the condition detection part 15.

Subsequently, the waveform information acquisition part 17a in a step S102 acquires a waveform detected by the waveform detection part 14. The waveform information acquisition part 17a in a step S103 adds a time stamp to acquired waveform and records it in the measured waveform data 16a as waveform information.

In parallel to steps S102 and S103, the status information acquisition part 17b performs steps S104 and S105. In the step S104, the status information acquisition part 17b acquires information indicating a condition of the user from the condition detection part 15. In the step S105, the status information acquisition part 17b adds a time stamp to acquired information and records it in the condition data 16b as condition information.

In a step S106, the waveform correction part 17d obtains waveform information recorded in the measured waveform data 16a and condition information recorded in the condition data 16b with time deviation being adjusted so that information within the same time period can be obtained. A magnitude of the time deviation is set based on a delay time from when a phenomena of the subject to be measured occurs to when a sensor outputs a signal according to the phenomena.

In a step S106, for example, waveform information indicating a waveform W1 as shown in FIG. 3 is obtained. Condition information obtained in the step S106 indicates a condition of the user at a period during which such a waveform is detected. A waveform W1 includes a noise component due to a condition indicated by conditional information.

Subsequently, in a step S107, the waveform correction part 17d performs a determination process based on the obtained condition information, as necessary. For example, the waveform correction part 17d foresees a moving condition of the user on a basis of a pattern of variation of a magnitude of an acceleration that is included in the obtained condition information. This process can be omitted in a case that condition information can be designated as it is when acquiring an artifact waveform from the artifact waveform data 16c.

Subsequently, in a step S108, the waveform correction part 17d causes the artifact waveform acquisition part 17c to acquire an artifact waveform corresponding to condition information (or the user's condition determined based on condition information) from the artifact waveform data 16c.

For example, in a step S108, a waveform W2 as shown in FIG. 3 is acquired as an artifact waveform. It is hard to use the waveform W2 as it is in order to remove a noise component from a waveform W1 because a scale of each of amplitude and a wavelength of the waveform W2 are distinct from a scale of that of the waveform W1.

In a step S109, the waveform correction part 17d adjusts a scale of amplitude and a wavelength of the acquired artifact waveform. For example, in a step S109, a waveform W3 can be obtained by adjusting a scale of each of amplitude and a wavelength of the waveform W2 shown in FIG. 3. A singular point of the waveform W1 is matched to a singular point of the waveform W2 in order to adjust the amplitude of the waveform W2. Such an adjustment allows for a use of the waveform W2 in order to remove a noise component.

Subsequently, in a step S110, the waveform correction part 17d removes a noise component from condition information using the adjusted artifact waveform. The waveform correction part 17d obtains a waveform W4, from which a noise component due to a condition has been removed, by dividing the waveform W3 shown in FIG. 3 by the waveform W1 shown in FIG. 3, for example.

Subsequently, in a step S111, the autonomic nerves diagnosis part 17e diagnoses autonomic nerves of the user on a basis of waveform information from which a noise component has been removed. In a step S112, the notice part 17f notifies the user of a result of a diagnosis.

Subsequently, in a step S113, the controller 17 determines whether or not to finish a diagnosis process. When not finishing the diagnosis process ("No" in a step S113), the controller 17 resumes steps following the steps S104 and steps following the step S104. When finishing the diagnosis process ("Yes" in a step S113), in a step S114, the controller 17 stops the waveform detection part 14 and the condition detection part 15.

The diagnosis process shown in FIG. 2 may be performed in a real time manner or in a butch manner. When performed in a real time manner, the steps S102 through S113 are performed in one second periods. When performed in a butch manner, the steps S102 and S103, and steps S104 and S105 are continuously performed. The steps S106 through S113 are performed at a predetermined timing.

As mentioned above, the mobile electronic device 10 removes a noise component due to a user's condition at detection from a waveform that has been detected from the user to diagnose autonomic nerves of the user. In this way, the mobile electronic device 10 can improve an accuracy of diagnosis of the user's autonomic nerves.

The embodiments disclosed in the present application can be modified without departing from the scope and the spirit of the invention. In addition, the embodiments and alternatives can be combined appropriately. For example, the above mentioned embodiments may be changed as follows.

For example, the mobile electronic device 10 may be configured in an extensible manner. Specifically, the mobile electronic device 10 is capable of adding any sensors and may be configured such that the waveform information acquisition part 17a or the status information acquisition part 17b obtains information detected by the added sensors as waveform information or condition information.

The mobile electronic device 10 may be configured such that the user is able to vary filtering coefficients, threshold value and the like used in a diagnosis process.

The components of the embodiments above mentioned may be dispersedly or integrally configured appropriately. A system including a server and a mobile electronic device 10 may be established such that a part of the mobile electronic device 10 is located in the server.

Figure 4:
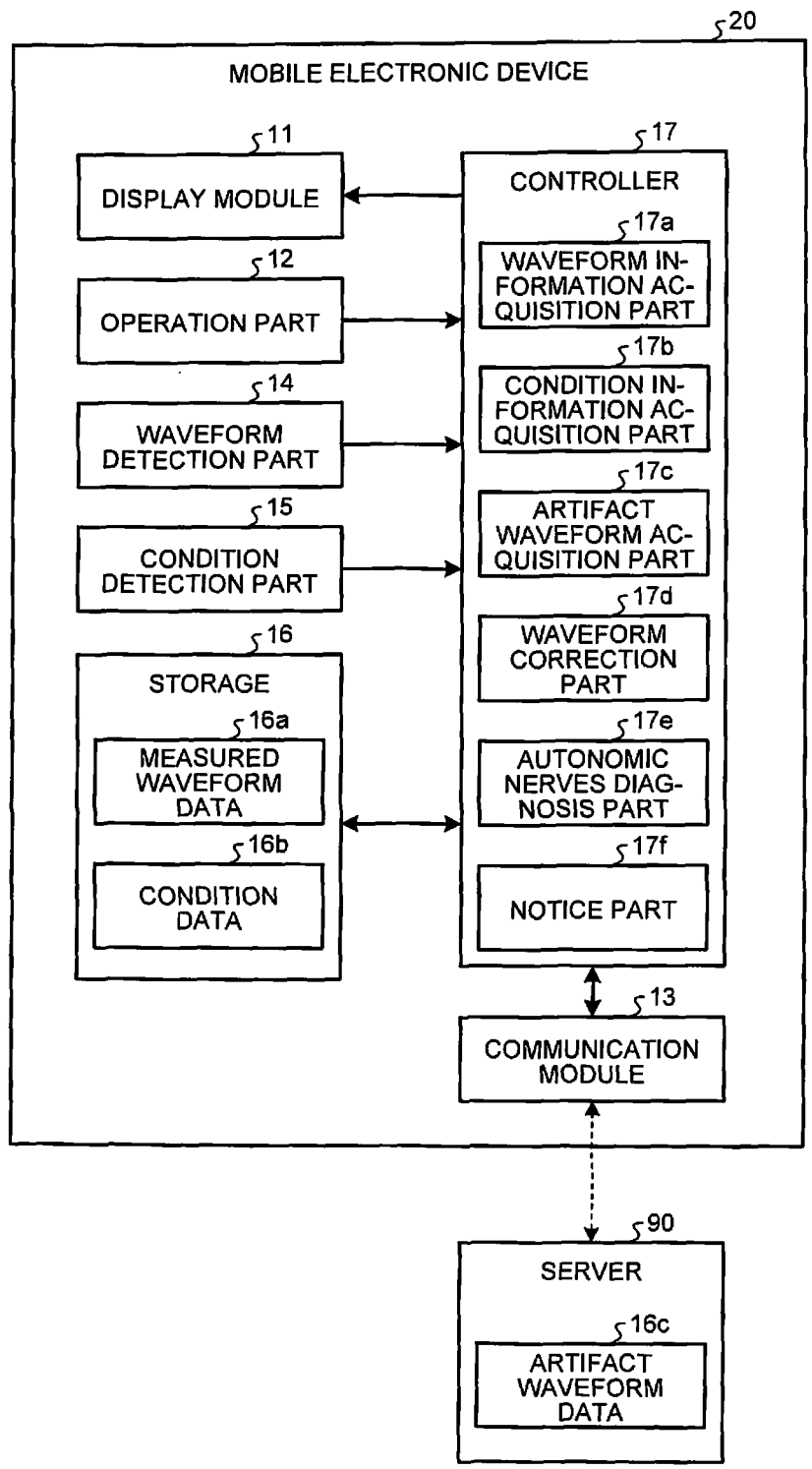
FIG. 4 is a diagram illustrating an exemplary configuration of a diagnosis system.

FIG. 4 is a diagram illustrating an exemplary construction of a diagnosis system. The diagnosis system shown in FIG. 4 includes a mobile electronic device 20 and a server 90. The server 90 stores artifact waveform data 16c. The mobile electronic device 20 is similar to the mobile electronic device 10 except for accessing to the artifact waveform data 16c stored in the server 90 via a communication through a communication module 13. In such a configuration, an effect similar to an effect of the mobile electronic device 10 can be accomplished.

Furthermore, as shown in FIG. 4, it is possible to utilize a memory area for another usage because the mobile electronic device 20 does not need to store the artifact waveform data 16c. Furthermore, as shown in FIG. 4, it is possible to easily make an addition or a change of an artifact waveform for example because the artifact waveform data 16c is centrally managed in the server 90.

Figure 5:
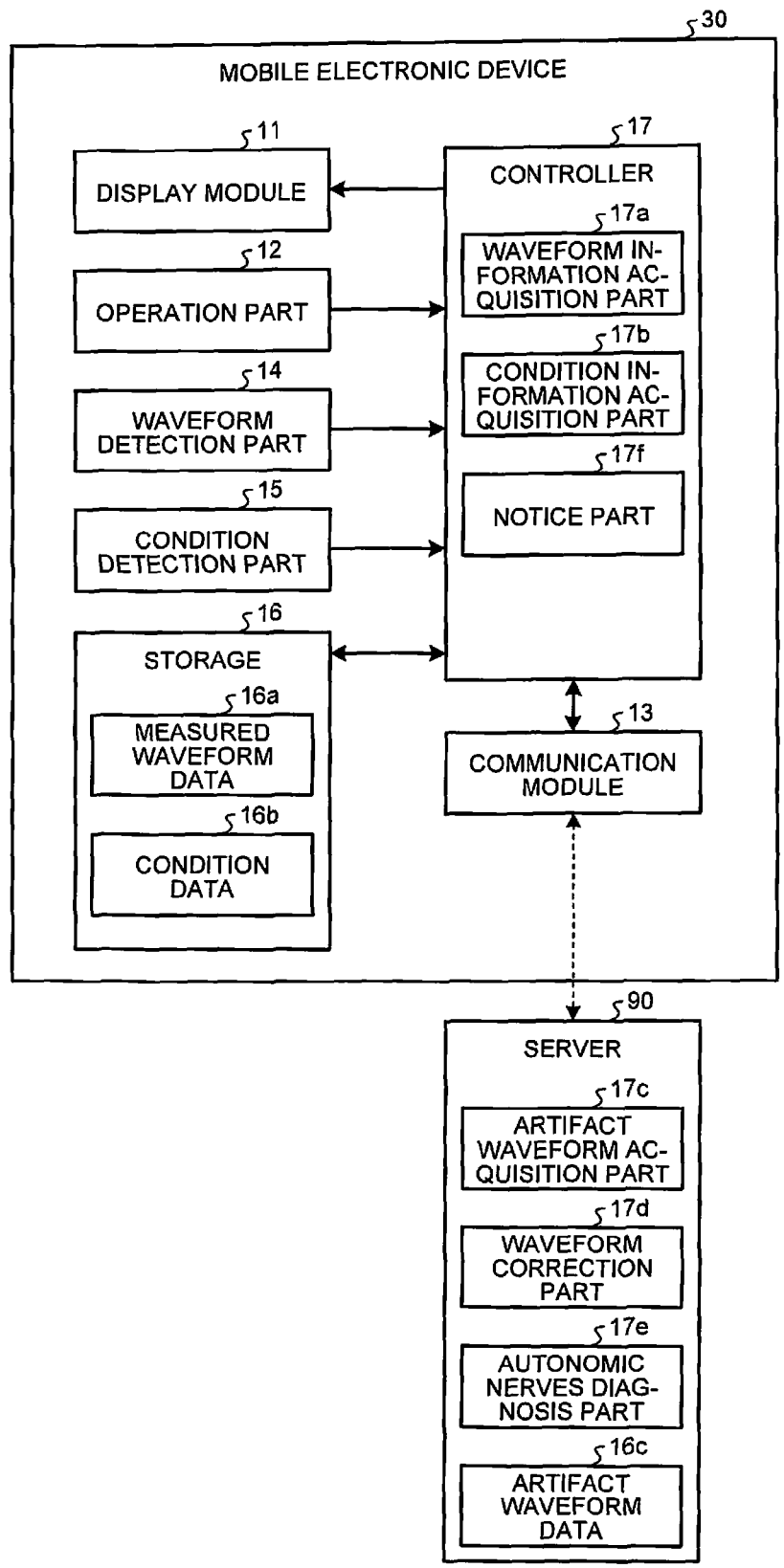
FIG. 5 is a diagram illustrating alternative exemplary configuration of a diagnosis system.

FIG. 5 is a diagram illustrating another exemplary construction of a diagnosis system. The diagnosis system shown in FIG. 5 includes a mobile electronic device 30 and a server 90. The server 90 stores artifact waveform data 16c, as well as includes an artifact waveform acquisition part 17c, a waveform correction part 17d, and an autonomic nerves diagnosis part 17e. The mobile electronic device 30 is similar to the mobile electronic device 10 except that the mobile electronic device 30 does not store the artifact waveform data 16c and does not included an artifact waveform acquisition part 17c, a waveform correction part 17d, and an autonomic nerves diagnosis part 17e.

As shown in FIG. 5, the mobile electronic device 30 transmits the measured waveform data 16a and the condition data 16b to a server 90 via a communication through a communication module 13. The server 90 performs a diagnosis process using the transmitted measured waveform data 16a and condition data 16b, and then responds a result to the mobile electronic device 30. The mobile electronic device 30 notifies a user of a responded reply. In such a configuration, an effect similar to an effect of the mobile electronic device 10 can be accomplished.

Furthermore, as shown in FIG. 5, it is possible to reduce a load of the mobile electronic device 30 because a main part of the diagnosis process is performed by the server 90. Furthermore, it is possible to easily make a renovation or an addition of function of a diagnosis process because a main part of the diagnosis process is performed by parts within the server 90.

Figure 6:
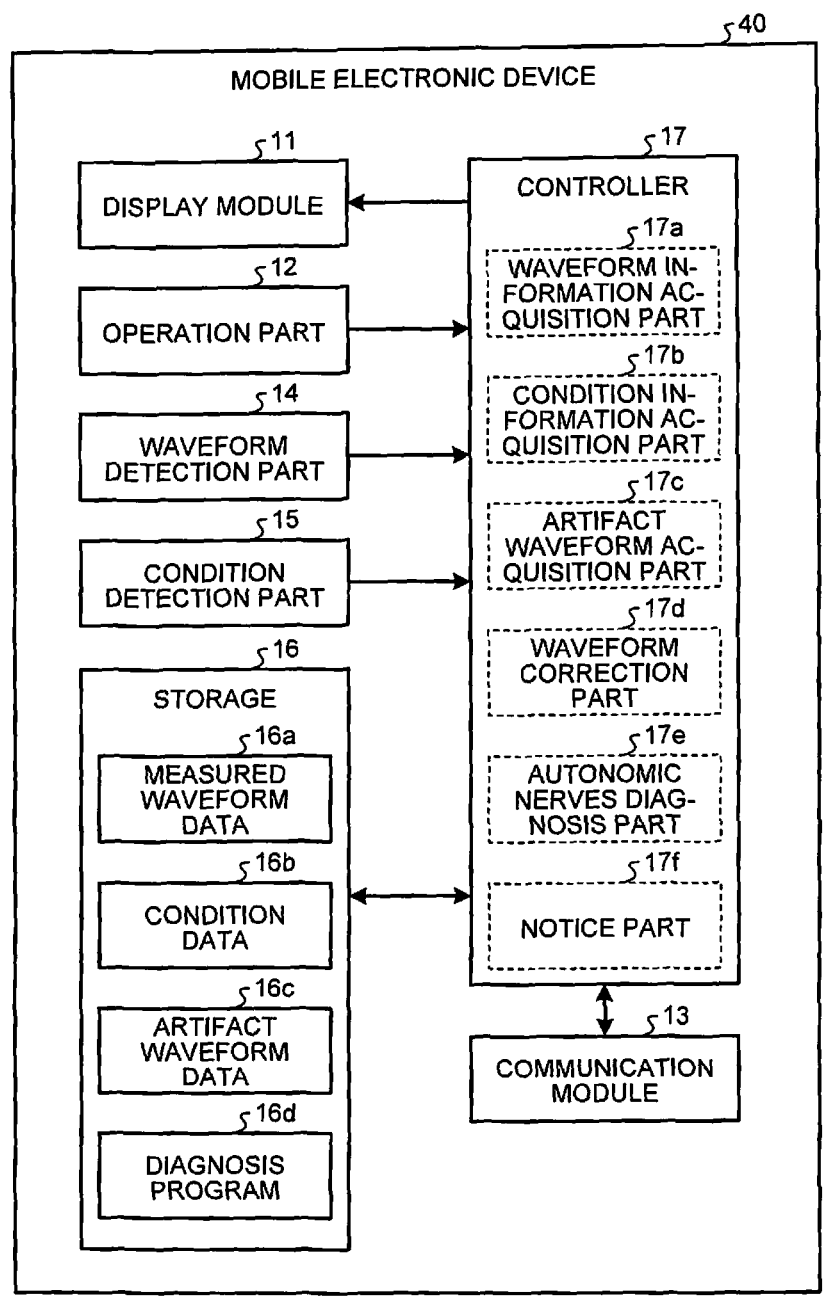
FIG. 6 is a diagram illustrating an exemplary configuration of a diagnosis process performed using software.

A diagnosis process may be performed using software. FIG. 6 is a diagram illustrating an exemplary configuration of a diagnosis process performed using software. A mobile electronic device 40 is similar to the mobile electronic device 10 except that a storage 16 stores a diagnosis program 16d.

In the mobile electronic device 40, a controller 17 causes a calculation processing unit to execute a diagnosis program 16d, so that functions including a waveform information acquisition part 17a, a status information acquisition part 17b, an artifact waveform acquisition part 17c, a waveform correction part 17d, an autonomic nerves diagnosis part 17e, and a notice part 17f are realized. In such a configuration, an effect similar to an effect of the mobile electronic device 10 can be accomplished. The diagnosis program 16d may be downloaded from another device. The diagnosis program 16d may be stored in a general purpose non-transitory memory medium.

when performing a diagnosis process using software, the mobile electronic device 40 may be configured so as to execute a program other than the diagnosis program 16d using the calculating processing unit. A program other than the diagnosis program 16d includes, for example, Social Networking Service (SNS) program, a mailing program, a schedule management program, a browser program and the like.

In such a case, the status information acquisition part 17b may acquire condition information indicating a condition of a user by monitoring the program being executed. The status information acquisition part 17b may derive information indicating a condition of a user from a message that a user has transmitted using the SNS program or the mailing program. For example, the status information acquisition part 17b derives information about a meal that a user is eating from the message and stores it as condition information.

The status information acquisition part 17b may derive information indicating a condition of a user from a schedule that the user has registered using a schedule management program. For example, the status information acquisition part 17b stores, as condition information, that a user is visiting the offices of a client company on a basis of a recorded schedule.

The status information acquisition part 17b may acquire information indicating a condition of a user on a basis of a WEB page that a user is browsing using a browser program. For example, the status information acquisition part 17b determines a kind of the WEB page by verifying an address of the WEB page being browsed with an access to a database, and then stores the kind of the WEB page as condition information.

In the above mentioned embodiments, although a mobile phone has been described as an example of a mobile electronic device, a device according to the claims attached hereto is not limited to the mobile phone. A device according to the claims attached hereto may be for example a smart phone, a tablet, laptop PC, a digital camera, a media player, an electronic book reader, a navigation system, or a gaming device.

While certain embodiments have been described in order to completely and definitely disclose any techniques according to the claims attached hereto, these embodiments have been presented by way of example only, and are not intended to limit the scope of the inventions. Indeed, the embodiments described herein may be embodied in a variety of other forms, substitutions and changes in the form of the embodiments described herein that may be made without departing from the spirit of the inventions. The accompanying claims and their equivalents are intended to cover such forms or modifications as would fall within the scope and spirit of the inventions.

The invention claimed is:
1. A mobile electronic device, comprising:
a waveform information acquisition part configured to
add a first time stamp to a waveform detected from a user, and
record the waveform with the first time stamp as waveform information;
a condition information acquisition part configured to
add a second time stamp to information indicating a condition of the user, and
record the information with the second time stamp as condition information;
an artifact waveform acquisition part configured to acquire, from artifact waveform data in which a condition and an artifact waveform are associated with each other and stored, the artifact waveform that corresponds to the condition of the user indicated by the condition information within the same time period as a time period of the waveform information;
a waveform correction part configured to correct the waveform information using the artifact waveform acquired by the artifact waveform acquisition part;
an autonomic nerves diagnosis part configured to diagnose autonomic nerves of the user using the waveform information corrected by the waveform correction part; and a notice part configured to notify the user of a result of diagnosing the autonomic nerves.

2. The mobile electronic device according to claim 1, wherein
the waveform correction part is configured to conform a scale of a wavelength of the artifact waveform to a scale of a wavelength of the waveform indicated by the waveform information on a basis of a singular point of the artifact waveform and a singular point of the waveform indicated by the waveform information.

3. The mobile electronic device according to claim 1, further comprising:
an acceleration sensor,
wherein the condition information acquisition part is configured to record, as the condition information,
either a direction and a magnitude of acceleration detected by the acceleration sensor,
or a moving condition of the user that is foreseen on a basis of the direction and the magnitude of acceleration detected by the acceleration sensor.

4. The mobile electronic device according to claim 1, further comprising:
a calculating processing unit configured to execute a program,
wherein the condition information acquisition part is configured to acquire information indicating a condition of the user by monitoring the program that is executed.

5. A non-transitory storage medium that stores a program causing, when executed by a mobile electronic device, the mobile electronic device to execute:
adding a first time stamp to a waveform detected from a user, and recording the waveform with the first time stamp as waveform information;
adding a second time stamp to information indicating a condition of the user and recording the information with the second time stamp as condition information;
acquiring, from artifact waveform data in which a condition and the artifact waveform are associated with each other and stored, an artifact waveform that corresponds to the condition of the user indicated by the condition information in the same time period as a time period of the waveform information;
correcting the waveform information using the artifact waveform;
diagnosing autonomic nerves of the user using the corrected waveform information; and
notifying the user of a result of diagnosing the autonomic nerves.

6. The mobile electronic device according to claim 1, wherein
the artifact waveform acquisition part is configured to, when the artifact waveform is associated with a plurality of kinds of the condition information,
determine a priority for each kind of the condition information, and
choose a combination of the condition information and the artifact waveform based on the priority.

7. The mobile electronic device according to claim 6, wherein
the artifact waveform acquisition part is configured to
evaluate an approximation of the condition information having higher priority in order, and
narrow the combination of the condition information and the artifact waveform based on the approximation.

8. The mobile electronic device according to claim 6, wherein
the artifact waveform acquisition part is configured to
acquire a total approximate value of the combination of the condition information and the artifact waveform by multiplying an approximate value that has been evaluated for the condition information by a weight allocated to each of the priorities of the condition information, and
choose the combination in order of the total approximation value.

9. The mobile electronic device according to claim 1, wherein
the stored artifact waveform data has been measured by a sensor that is different from a sensor that detects the waveform of the user.

10. The mobile electronic device according to claim 2, wherein
the artifact waveform and the singular point are calculated using a Fourier transformation, a fast Fourier transformation or a wavelet transformation.

11. The mobile electronic device according to claim 1, wherein
the waveform correction part is configured to adjust a time deviation between the waveform information and the condition information.

12. The mobile electronic device according to claim 1, wherein
the waveform correction part is configured to remove a noise component from the waveform information using the artifact waveform.

13. The diagnosis system according to claim 1, wherein the notice part is configured to notify the user of the result of diagnosing the autonomic nerves, by causing the result of diagnosing the autonomic nerves to be displayed on a display.

14. A diagnosis system, comprising:
a memory configured to store an artifact waveform data in which an activity information indicating an activity status of a person and an artifact waveform ascribed to the activity status indicated by the activity information are associated with each other; and
a controller communicatively or electronically coupled to the memory, wherein the controller is configured to:
add a time stamp to a waveform detected from a user in a predetermined time period to obtain a stamped waveform information,
add another time stamp to activity information indicating an activity status of the user in the predetermined time period to obtain a stamped activity information,
acquire, from the artifact waveform data, the artifact waveform that corresponds to the activity information indicating the activity status indicated by the stamped activity information,
correct the stamped waveform information using the artifact waveform acquired from the artifact waveform data to obtain corrected waveform information,
diagnose autonomic nerves of the user using the corrected waveform information, and
notify the user of a result of diagnosing the autonomic nerves.

15. The diagnosis system according to claim 14, further comprising:
another memory configured to store the stamped waveform information and the stamped activity information, wherein the controller is communicatively or electronically coupled to the another memory, and further configured to:
write the stamped waveform information to the another memory, and
write the stamped activity information to the another memory.

16. The diagnosis system according to claim 14, further comprising:
a communication circuit electrically coupled to the controller,
wherein the controller is further configured to cause the communication circuit to communicate wirelessly with an external device.

17. The diagnosis system according to claim 16, wherein the controller is further configured to cause the communication circuit to send the result of diagnosing the autonomic nerves to the external device.

18. The diagnosis system according to claim 14, wherein the waveform includes at least one of a waveform of pulse wave and a waveform indicating a variation of a heart rate.

19. The diagnosis system according to claim 14, wherein the waveform is measured by at least one of a camera, a heart rate sensor and a photoelectric pulse wave counter.

20. The diagnosis system according to claim 14, wherein the activity status of the user is foreseen based on a result detected by at least one of an acceleration sensor, a barometer, a Global Positioning System receiver, an illuminance sensor, a temperature sensor and an electrostatic capacitive touch sensor.

* * * * *